United States Patent
Henderson

(10) Patent No.: US 9,446,089 B1
(45) Date of Patent: Sep. 20, 2016

(54) OIL BLEND FOR SKIN TREATMENT

(71) Applicant: Aja Henderson, Huntsville, AL (US)

(72) Inventor: Aja Henderson, Huntsville, AL (US)

(*) Notice: Subject to any disclaimer, the term of this patent is extended or adjusted under 35 U.S.C. 154(b) by 321 days.

(21) Appl. No.: 14/322,395

(22) Filed: Jul. 2, 2014

Related U.S. Application Data

(63) Continuation-in-part of application No. 13/594,008, filed on Aug. 24, 2012, now Pat. No. 8,932,656.

(60) Provisional application No. 61/843,257, filed on Jul. 5, 2013.

(51) Int. Cl.
| | |
|---|---|
| *A01N 65/00* | (2009.01) |
| *A61K 36/889* | (2006.01) |
| *A61K 36/61* | (2006.01) |
| *A61K 31/355* | (2006.01) |
| *A61K 36/28* | (2006.01) |
| *A61K 35/12* | (2015.01) |
| *A61K 36/63* | (2006.01) |
| *A61K 36/36* | (2006.01) |

(52) U.S. Cl.
CPC .......... *A61K 36/889* (2013.01); *A61K 31/355* (2013.01); *A61K 35/12* (2013.01); *A61K 36/28* (2013.01); *A61K 36/36* (2013.01); *A61K 36/61* (2013.01); *A61K 36/63* (2013.01)

(58) Field of Classification Search
CPC .................................................... A61K 36/00
USPC ........................................................ 424/725
See application file for complete search history.

(56) References Cited

U.S. PATENT DOCUMENTS

| | | | |
|---|---|---|---|
| 4,454,159 A | 6/1984 | Musher | |
| 4,784,849 A | 11/1988 | Tutsky | |
| 5,578,312 A | 11/1996 | Parrinello | |
| 6,627,178 B1 | 9/2003 | Cauthon | |
| 6,716,441 B1 | 4/2004 | Osborne | |
| 7,115,287 B2 | 10/2006 | Froggatt | |
| 7,241,456 B2 | 7/2007 | Vromen | |
| 7,357,950 B2 | 4/2008 | Mazzio | |
| 7,390,507 B2 | 6/2008 | Ruwart | |
| 7,879,344 B2 | 2/2011 | Feldkamp | |
| 2002/0044977 A1 | 4/2002 | Close | |
| 2004/0081681 A1 | 4/2004 | Vromen | |
| 2008/0145443 A1 | 6/2008 | Langolf | |
| 2008/0206155 A1 | 8/2008 | Tamarkin | |
| 2008/0233060 A1 | 9/2008 | Grune | |
| 2008/0234224 A1 | 9/2008 | Kamachi | |
| 2008/0311234 A1 | 12/2008 | Yoneda | |
| 2009/0123504 A1 | 5/2009 | Feldkamp | |
| 2010/0247563 A1 | 9/2010 | Hines | |
| 2010/0303854 A1 | 12/2010 | Hines | |
| 2011/0008474 A1 | 1/2011 | Boegli | |
| 2011/0097279 A1 | 4/2011 | Tamarin | |
| 2011/0136210 A1 | 6/2011 | Benjamin | |

FOREIGN PATENT DOCUMENTS

WO    WO2010006376    1/2010

OTHER PUBLICATIONS

Bedi et al. (2002) Arch Dermatol. vol. 138. pp. 232-242.
Aburjai et al. (2003) Phylother. Res. 17, 987-1000.
Hempel (1999) Acta Hort. 503: 15-20.
Priest, D. Medicinal and Aromatic Plants—Industrial Proviles. (1999), 9, (Tea Tree), 203-206. Publisher: (Harwood Academical Publishers).
Lee et al. (2010) J. Vet. Sci. 11(1): 35-41.

*Primary Examiner* — Michael Meller
(74) *Attorney, Agent, or Firm* — CreatiVenture Law; Linda L Lewis

(57) ABSTRACT

An anhydrous blend of oils suitable for treating or preventing skin ailments, such as eczema, and for soothing the skin. The blend includes virgin coconut oil, extra virgin olive oil, jojoba oil, calendula oil, vitamin E oil, tea tree oil, German chamomile extract and lanolin. The blend does not contain water soluble actives and is essentially free from corn oil and soy oil.

1 Claim, No Drawings

OIL BLEND FOR SKIN TREATMENT

CROSS-REFERENCE TO RELATED APPLICATION

The present application is a continuation-in-part application based on U.S. application Ser. No. 13/594,008 filed Aug. 24, 2012, which is hereby incorporated by reference, and claims the benefit of provisional patent application 61/536,720 filed Sep. 20, 2011 and provisional patent application 61/843,257, filed Jul. 5, 2013, which are hereby incorporated by reference.

STATEMENT REGARDING FEDERALLY SPONSORED RESEARCH

Not Applicable.

APPENDIX

Not Applicable.

BACKGROUND OF THE INVENTION

1. Field of the Invention

The present invention is directed to a unique anhydrous blend of oils for treating and soothing skin.

2. Related Art

Eczema is the term used to describe a number of skin conditions including contact dermatitis, atopic dermatitis and seborrhoeic dermatitis. These conditions are characterized by pruritus (itchiness), erythema (redness), excoriation (scratches, scabs), induration (swelling) and papulation (bumpiness) of the skin. Causes can range from allergic reactions to external substances, as in contact dermatitis, to internal causes as in atopic dermatitis or a yeast infection as in seborrhoeic dermatitis. Contact dermatitis occurs after exposure to substances such as urushiol oil from the poison ivy plant. Symptoms can include red, extremely itchy rashes, fluid filled blisters and swelling. Treatment for contact dermatitis involves removing the causative agent, then treating the remaining symptoms. Drying agents, such as calamine lotion are used to dry fluid filled blisters. Therapies include topical anti-inflammatory corticosteroids and numbing agents to help relieve swelling and itch. Seborrhoeic dermatitis can be treated with dandruff medications, anti-fungals and corticosteroids.

Although the exact cause of atopic dermatitis is unknown, it is thought to be the result of a disorder of the immune system and appears to have a genetic component, often occurring in great frequency in certain families and ethnic groups. It often presents during infancy and sometimes disappears by adulthood. In some cases, it presents for the first time in adulthood. It can cause considerable distress from constant itchiness, dry skin, unsightly rashes and, in the worst cases, can cause debilitation and require hospitalization. There is no known cure for atopic dermatitis. Treatments consist of moisturizing lotions, occlusive dressing for extremely dry patches, topical anti-inflammatory corticosteroids and numbing agents. OTC strength preparations of these therapies usually have a minimal effect. Prescription strength corticosteroids are the most commonly prescribed therapies but can have serious detrimental side effects such as thinning of the skin, stretch marks or eye damage often necessitating discontinuation of the treatment. Numbing agents and antihistamines provide minimal relief in the majority of moderate to severe clinical cases. Soothing emollients, phenol, menthol and camphor can provide some short term relief for mild pruritus. UVB light therapy is commonly used to treat severe cases of eczema with a high rate of effectiveness, although undesirable side effects can occur such as an increased risk of developing skin cancer as well as undesirable phototoxic reactions (see for example, Marks, J Dermatol Treat 1:233-234, 1989).

Typically, a topical cream, ointment, lotion or paste is applied to the skin. For the topical application method to be effective, the creams or ointments need to be substantive, i.e., they need to coat the target surface and remain at the site of application. Most current topical delivery systems are O/W or W/O (oil in water or water in oil) emulsions. These emulsions generally have inferior solubility properties, hence they are easily removed by moisture (from washing, perspiration or other bodily exudates), or rubbing against clothing, and often fail to provide long-lasting benefits to the site of application.

Water-free creams or ointments are also known. Typically, these creams or ointments use oleaginous base such as petrolatum to provide the substantively of the creams or ointments for a long-lasting coating of the target areas.

Less common delivery systems are substantially anhydrous, oleaginous compositions. The oleaginous compositions are generally more water insoluble than the O/W or W/O emulsions; thus, they may serve as reservoirs from which the active ingredients are continuously delivered. However, they may not be efficient in delivering the water soluble active ingredients. This is because the skin care actives are water-soluble and exist as solid particles or powders in the oleaginous composition. These solid particles or powders are entrapped in the substantially anhydrous oleaginous base and cannot be easily released from the composition to the target skin surface. Moreover, even when these active ingredients are in contact with the target skin surface, they may not function efficiently in their solid form.

The present invention is directed to a substantially anhydrous of blend of oils for treating and soothing skin that overcomes the disadvantages of the related art compositions. Because the claimed composition is a mixture of oils, it resists removal with water or bodily fluids. Since it is essentially free of water-soluble actives in the oil blend, there is no failure of the composition in delivering the drug active. The unique blend of oils provides soothing of irritated skin with anti-bacterial and anti-fungal actives that are readily available to heal the skin.

SUMMARY OF THE INVENTION

The present invention is directed to a substantially anhydrous blend of oils comprising coconut oil, tea tree oil, vitamin E, German chamomile extract, and lanolin wherein the blend does not contain water soluble actives. Substantially anhydrous means that at 70 degrees F., there is no separate water phase visible in the blend. To not contain water soluble actives means that at 70 degrees F., there are no visible particles of water soluble actives present in the blend. In an embodiment of the invention, the blend of oils comprises virgin coconut oil, extra virgin olive oil, jojoba oil, calendula oil, vitamin E oil, tea tree oil, German chamomile extract, and lanolin. Preferably, the vitamin E and the blend itself is essentially free from corn oil and soy oil.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses. The preferred ingredients used in this blend of oils are pure and organic. As different blends were made and tested this was found to be critical to the effectiveness of the desired blend. Tea tree oil and lavender oil are anti-bacterial. Coconut oil and tea tree oil are anti-fungal. Olive oil, jojoba oil and calendula oil are soothing to the skin. German chamomile extract provides mild pain relief. Vitamin E promotes healing.

Coconut oil is anti-fungal and therefore the primary component. Coconut oil is solid below 74 degrees F. and a solid or semi-solid mixture is undesirable. The blend was varied to maximize the amount of coconut oil while keeping the mixture a liquid at room temperature. It was determined that up to about 38 vol. % coconut oil can be used without the blend solidifying, which in turn resulted in separation of the oils into layers. Below about 70 degrees F., the product began to solidify, but no separation into layers was observed. Above about 70 degrees F., the blend is liquid and homogeneous. A preferred range of coconut oil is from about 20 to 30 vol. %. A more preferred range is from about 22 to 27 vol. %.

The remaining approximately 60 vol. % of the mixture is made of extra virgin olive oil, jojoba oil, calendula oil, vitamin E oil, tea tree oil, German chamomile extract and lanolin. The extra virgin olive oil, jojoba oil and calendula oil act as carriers for the other oils and are therefore optional. Additionally, the calendula oil has anti-inflammatory properties However, adding one or more of them to the blend does provide a product that is easier to handle and store. In an embodiment, the extra virgin olive oil is present from about 7 to 17 vol. %, the jojoba oil is present from about 30 to 40 vol. % and the calendula oil is present from about 7 to 17 vol. %. In a preferred embodiment, equal amounts of olive oil and calendula oils produced the best results.

Tea tree oil is known to be anti-bacterial, but can be irritating if applied directly to the skin directly, so very small amounts are used in the oil blend. The preferred concentration is about less than about 3.0 vol. %. Preferably, it is from about 0.01 vol. % to about 3.0 vol. % in the blend. Optionally, lavender oil can be added for its antibacterial properties and also for its fragrant smell. Baby products may contain lavender because it has a calming effect on infants. German chamomile extract is added from about 0.1 vol. % to 10.0 vol. % and vitamin E was added at 0.1 vol. % to 10.0 vol. %. The German chamomile extract provides pain relief and the vitamin E helps heal the skin while the other ingredients fought the cause of the rash. Lanolin is added from about 1 to 10 vol. % to provide a barrier that holds in the moisture.

Vitamin E was found to be less effective than a preferred all natural vitamin E that is essentially free of corn oil and soy oil. A commercial source of such oil is UNIQUE E a trademark of A.C. Grace and sold by Vitamin Shoppe. A preferred vitamin E formula is devoid of all fillers, additives, wheat, gluten, corn oil or soy oil. The preferred vitamin E contains d-alpha tocopherol. Oil blends made with the vitamin E essentially free of corn oil and soy oil are very effective in treating eczema.

This blend of oils is suitable for soothing and treating skin. It is particularly considered efficacious in treating eczema or other rashes. It is also suitable for treating or preventing skin rashes such as eczema, dry skin or other skin conditions.

The oil is used by applying directly to the skin with rubbing or massaging. The following examples are for illustrative purposes only and in no way limit the scope of the invention.

Example 1 was made by blending together the following oils:

Example 1

Coconut Oil 25.64%
Jojoba Oil 35.90%
Olive Oil 12.82%
Calendula Oil 12.82%
Chamomile (4% extract in Jojoba oil) 3.85%
Tea Tree Oil 2.56%
Vitamin E Oil* 3.85%
Lanolin 2.56%
*Essentially free of fillers, additives, wheat gluten, corn oil and soy oil.

The above-listed ingredients were warmed above 70 degrees F. and mixed together. The oils were substantially anhydrous and the mixture, when cooled to about 70 degrees F. was liquid and homogeneous. There were no visible particles due to water soluble actives.

Example 2

The formula was the same as Example 1, except that twice the amount of tea tree oil was used. The blend relieved itching, but had an unpleasant smell. The amount of tea tree oil was reduced, and the performance of the product was not diminished.

Application 1

The oil of Example 1 was applied to the skin of a patient with a rash due to poison ivy exposure. The patient experienced immediate relief from itching.

Application 2

The oil of Example 1 was applied to the skin of a patient suffering from eczema. It was as effective in treating the eczema as a steroid cream.

Application 3

The oil of Example 1 was applied to the skin of a child patient suffering from severe eczema. There was relief from itching in 24 hours and the rash was completely gone in 5 days.

Application 4

The oil of Example 1 was applied to the skin of a child patient suffering from eczema on his elbows and knees. There was immediate relief from itching.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:
1. A composition for treating eczema consisting essentially of 25.64% of Coconut Oil, 35.90% of Jojoba Oil, 12.82% of Olive Oil, 12.82% of Calendula Oil, 3.85% Chamomile extract, 2.56% of Tea Tree Oil, 3.85% of Vitamin E Oil, and 2.56% Lanolin.

* * * * *